US012383732B2

(12) United States Patent  
Albeck et al.

(10) Patent No.: US 12,383,732 B2  
(45) Date of Patent: Aug. 12, 2025

(54) SYSTEM AND METHOD FOR COCHLEAR IMPLANT STIMULATION

(71) Applicants: Nurotone Medical Ltd., Rosh Ha'Ayin (IL); NORTHWESTERN UNIVERSITY, Evanston, IL (US)

(72) Inventors: Dan David Albeck, Givat Shmuel (IL); Claus-Peter Richter, Skokie, IL (US)

(73) Assignees: Nurotone Medical Ltd., Rosh Ha'Ayin (IL); NORTHWESTERN UNIVERSITY, Evanston, IL (US)

( * ) Notice: Subject to any disclaimer, the term of this patent is extended or adjusted under 35 U.S.C. 154(b) by 944 days.

(21) Appl. No.: 17/268,400

(22) PCT Filed: Aug. 14, 2019

(86) PCT No.: PCT/IL2019/050911  
§ 371 (c)(1),  
(2) Date: Feb. 12, 2021

(87) PCT Pub. No.: WO2020/035861  
PCT Pub. Date: Feb. 20, 2020

(65) Prior Publication Data  
US 2021/0339011 A1  Nov. 4, 2021

Related U.S. Application Data

(60) Provisional application No. 62/718,569, filed on Aug. 14, 2018.

(51) Int. Cl.  
*A61N 1/36* (2006.01)  
*A61N 1/05* (2006.01)  
*A61N 5/06* (2006.01)

(52) U.S. Cl.  
CPC ....... *A61N 1/0541* (2013.01); *A61N 1/36038* (2017.08); *A61N 1/36171* (2013.01);  
(Continued)

(58) Field of Classification Search  
CPC .............. A61N 1/0541; A61N 1/36038; A61N 1/36171; A61N 1/36175; A61N 1/36164; A61N 5/0622  
See application file for complete search history.

(56) References Cited

U.S. PATENT DOCUMENTS 8,346,368 B2    1/2013  Killian  
2006/0161227 A1* 7/2006  Walsh, Jr. ............ A61N 5/0622  
607/55  
(Continued)

FOREIGN PATENT DOCUMENTS

CN    102 525 734    7/2012  
CN    103 140 260    6/2013  
(Continued)

OTHER PUBLICATIONS

International Search Report for Application No. PCT/IL2019/050911 dated Nov. 28, 2019.

*Primary Examiner* — Eugene T Wu  
(74) *Attorney, Agent, or Firm* — Bell & Manning, LLC

(57) ABSTRACT

Disclosed is a method of selecting stimulations for a cochlear implant or an auditory implant. The method may include: capturing an acoustical signal; dividing the acoustical signal into a plurality of frequency bands; determining a mean acoustical energy for each frequency band; for each frequency band: comparing the mean acoustical energy with the mean acoustical energy determined for neighboring frequency bands; merging neighboring frequency bands having a difference between the mean acoustical energies that is less than an acoustical energy threshold value; selecting one or more types of stimulation to be applied to one or more locations in a cochlea or along an auditory nerve based on bandwidths of each frequency band. The one or more types of stimulation may be selected from: electrical stimulation, optical stimulation and opto-electrical stimulation,  
(Continued)

and the one or more locations in cochlea or along the auditory nerve may correspond to specific frequencies of the acoustical signal.

7 Claims, 8 Drawing Sheets

(52) U.S. Cl.
CPC ...... *A61N 1/36175* (2013.01); *A61N 1/36164* (2013.01); *A61N 5/0622* (2013.01)

(56) References Cited

U.S. PATENT DOCUMENTS

| | | |
|---|---|---|
| 2011/0077712 A1 | 3/2011 | Killian |
| 2013/0023960 A1 | 1/2013 | Stafford |
| 2013/0023967 A1* | 1/2013 | Stafford ............... A61N 5/0622 607/88 |
| 2014/0105434 A1 | 4/2014 | Goorevich |
| 2015/0343217 A1 | 12/2015 | Smith |

FOREIGN PATENT DOCUMENTS

| | | |
|---|---|---|
| CN | 103 190 966 | 7/2013 |
| CN | 104 968 391 | 10/2015 |
| CN | 105 007 982 | 10/2015 |
| CN | 106 537 940 | 3/2017 |
| CN | 107 708 794 | 2/2018 |
| CN | 107 924 072 | 4/2018 |

\* cited by examiner

Fig. 5A
Fig. 5B
Fig. 5C

SYSTEM AND METHOD FOR COCHLEAR IMPLANT STIMULATION

CROSS-REFERENCE TO RELATED APPLICATIONS

This application is a National Phase Application of PCT International Application No. PCT/IL2019/050911, International Filing Date Aug. 14, 2019, claiming the benefit of U.S. Provisional Patent Application No. 62/718,569, filed Aug. 14, 2018, which are hereby incorporated by reference.

GOVERNMENT INTEREST STATEMENT

This invention was made with US government support under Grant No. R01DC011855 awarded by the USA National Institutes of Health. The US government has certain rights in the invention.

FIELD OF THE INVENTION

The present invention relates to neural stimulations in cochlear implant. More particularly, the present invention relates to systems and methods for selecting neural stimulations for a cochlear implant.

BACKGROUND OF THE INVENTION

Cochlear implant (CI) is surgically implanted neuroprosthetic device that provide a sense of sound to a person with moderate to profound sensorineural hearing loss. Commercially available CIs include an array of electrical contacts (electrodes) which is surgically inserted into the cochlea (scala tympani), to stimulate the cochlear nerve. Most commercially available CIs include 12-22 electrical contacts. The contact location of each electrical contact along the cochlear spiral is selected in order to stimulate a different part of the cochlear nerve, which corresponds to a different acoustic frequency band. The CI also includes a microphone configured to capture an acoustical signal (e.g., speech, music and the like) and a sound processor that is configured to divide the acoustical signal into a number of frequency bands corresponding to the number of electrical contacts of the CI with the cochlear spiral. The processor than determines to which electrical contact and at which intensity an electrical current should be delivered in order to stimulate the corresponding location along the cochlear nerve.

However, a wide section of the cochlear nerve is stimulated by each of the electrical contacts because of the wide spreading of the electrical current in the tissue resulting in up to 8 independent frequency channels along the cochlea.

Some improvements were made to increase the spatial resolution of the electrical stimulation like peri-modiolar electrode design which positions the electrode and its electrical contacts closer to the cochlear neurons, and current steering that uses interaction and interference between neighboring channels to evoke a percept, which is between the sites of the electrode contacts used to deliver the current. This strategy increases the number of pitches a CI user can perceive.

Neural stimulation with photons has been proposed for a next generation of neural prostheses including CIs. The potential benefit of photonic stimulation is its spatially selective activation of small neuron populations. Stimulating smaller spiral ganglion neuron (SGN) populations along the cochlea provides a larger number of independent channels to encode the acoustic information. Hearing could be restored at a higher fidelity and performance in noisy listening environments, as well as, music appreciation is likely to improve. The required energy to stimulate nerves depends on the stimulation technology. Electrical current is the most efficient one, while optical stimulation requires higher stimulation energies and additionally the limited efficiency of converting electricity to stimulation light increases the consuming energy and the heat dissipation.

There are two known methods for optical neural stimulation, optogenetics and infrared neural stimulation (INS). Optogenetics requires a viral vector to express photosensitive ion channels in the membrane of the target neurons. INS does not require such treatment because during INS, the fluid in the target tissue absorbs the photons and the energy is converted into heat. The result is a rapid temperature change (dT/dt) that leads to capacitive changes of the cell membrane, activation of temperature sensitive ion channels, such as transient receptor potential channels, changes in gating dynamics of potassium and sodium channels, modulations of GABAergic transmission (e.g., pertaining to or affecting the neurotransmitter GABA (Gamma-Aminobutyric Acid). A synapse is GABAergic if it uses GABA as its neurotransmitter), activation of a second messenger, calcium release in the cell, or to mechanical events such as stress relaxation waves with measurable pressure.

An attempt was made to gain the high resolution of the optical stimulation while minimizing the required energy through combined electrical and optical stimulations. In this attempt, reduction of power requirements was obtained with sub-threshold electrical stimulation combined with supra threshold optical stimulation. The benefit of this method was the reduction of the energy required for stimulation and the reduced dissipated heat especially from the light emitters, while having high resolution stimulation defined by the spread of the stimulation light. Spatially more confined stimulation was result in more independent channels with improved speech recognition and music appreciation. However, the suggested method still requires the use of a large number of light emitters for each received acoustical signal.

Therefore, it is beneficial to use electrical and optical stimulation in a way that may allow further reduction of the energy consumption without derogating from the hearing experience provided to the user (e.g., speech recognition and music appreciation).

SUMMARY OF THE INVENTION

Some aspects of the invention may include method of selecting stimulations for a cochlear implant. In some embodiments, the method may include: capturing an acoustical signal; dividing the acoustical signal into a plurality of frequency bands; determining a mean acoustical energy for each frequency band; for each frequency band: comparing the mean acoustical energy with the mean acoustical energy determined for neighboring frequency bands; merging neighboring frequency bands having a difference between the mean acoustical energies that is less than an acoustical energy threshold value; selecting one or more types of stimulation to be applied to one or more locations in a cochlea based on bandwidths of each frequency band. In some embodiments, the one or more types of stimulation may be selected from: electrical stimulation, optical stimulation and opto-electrical stimulation, and the one or more locations in cochlea may correspond to specific frequencies of the acoustical signal.

In some embodiments, the method may further include continue merging neighboring frequency bands if the merged frequency bands have a bandwidth lower or equal to a bandwidth limit value. In some embodiments, bandwidth limit value may be equal to a bandwidth of frequencies corresponding to neurons effected from the current spread of electrical stimulation. In some embodiments, selecting electrical stimulation is for merged neighboring frequency bands. In some embodiments, selecting one of: optical stimulation and opto-electrical stimulation is for the unmerged frequency bands. In some embodiments, selecting electrical stimulation is for merged neighboring frequency bands having a combined frequency bandwidth higher than a bandwidth threshold value. In some embodiments, selecting one of: optical stimulation and opto-electrical stimulation is for merged frequency bands having a combined frequency bandwidth lower than a bandwidth threshold value.

In some embodiments, the opto-electrical stimulation may include generating at a substantially same location an electrical stimulation and an optical stimulation, wherein each one of the electrical stimulation and the optical stimulation has an intensity level which is below a stimulation level. In some embodiments, the number of frequency bands is determined by the maximal number of light emitters and electrode contacts available for stimulation. In some embodiments, a wavelength of the optical simulation may be 400-1064 nm for optogenetics stimulation. In some embodiments, a wavelength of the optical simulation may be 1064-2500 nm for infrared neural stimulation.

Some other aspects of the invention may be directed to a method of generating stimulations for a cochlear implant. In some embodiments, the method may include capturing an acoustical signal; dividing the acoustical signal into a plurality of frequency bands; determining a mean acoustical energy for each frequency band; for each frequency band, comparing the mean acoustical energy with the mean acoustical energy determined for neighboring frequency bands; merging neighboring frequency bands having a difference between the mean acoustical energy that is less than an acoustical energy threshold value; selecting one or more types of stimulation to be applied to one or more locations in a cochlea based on bandwidths of each frequency band; and generating the selected one or more types of stimulation at the one or more locations in cochlea using at least one of: one or more electrical contacts and one or more light emitters.

In some embodiments, the one or more types of stimulation may be selected from: electrical stimulation, optical stimulation and opto-electrical stimulation, and the one or more locations in cochlea may correspond to specific frequencies of the acoustical signal.

In some embodiments, the method may further include continue merging neighboring frequency bands if the merged frequency bands may have a bandwidth lower or equal to a bandwidth limit value. In some embodiments, the bandwidth limit value may be equal to a bandwidth of frequencies correspond to neurons effected from the current spread of electrical stimulation.

Some embodiments of the invention may be directed to a method of selecting stimulations for an auditory implant. In some embodiments, the method may include: capturing an acoustical signal; dividing the acoustical signal into a plurality of frequency bands; determining a mean acoustical energy for each frequency band; for each frequency band: comparing the mean acoustical energy with the mean acoustical energy determined for neighboring frequency bands; merging neighboring frequency bands having a difference between the mean acoustical energies that is less than an acoustical energy threshold value; selecting one or more types of stimulation to be applied to one or more locations along an auditory nerve based on bandwidths of each frequency band. In some embodiments, the one or more types of stimulation may be selected from: electrical stimulation, optical stimulation and opto-electrical stimulation, and the one or more locations in along the auditory nerve may correspond to specific frequencies of the acoustical signal.

In some embodiments, the method may further include continue merging neighboring frequency bands if the merged frequency bands may have a bandwidth lower or equal to a bandwidth limit value.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 5A-5C are illustrations of an acoustical frequency spectrum and the division of the spectrum into frequency bends in accordance with some embodiments of the present invention;

Figure 1:
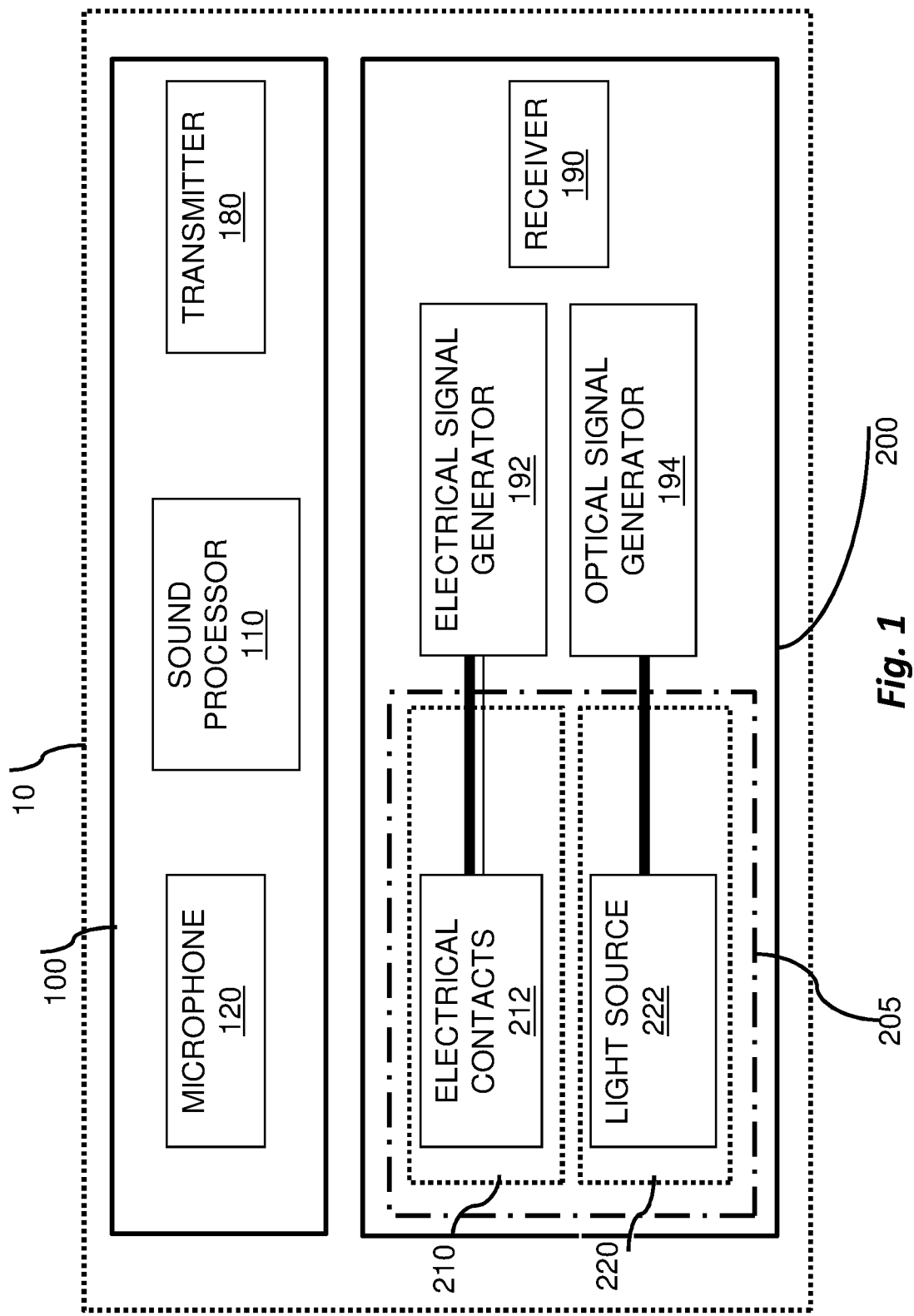
FIG. 1 shows a block diagram of an exemplary CI device, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining,"

"establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some aspects of the invention may be related to a computerized coding method of selecting stimulations for a CI. A CI according to embodiments of the invention may include both electrode with electrical contacts for providing electrical stimulations and optrode with light emitters for providing optical stimulations. The electrical contacts and light emitters may be placed at various locations along the cochlea. In some embodiments, a stimulation of an acoustical signal captured by a microphone of the CI may be divided between the electrical contacts and the light emitters, in order to provide high quality hearing experience at relatively low stimulation energy, low heat consumption and low energy consumption.

Reference is made to FIG. 1, which shows a block diagram of an exemplary device 10 (e.g., an IC device) according to some embodiments of the invention. Device 10 may include a controller 100 and an implant 200. Controller 100 may include: a sound processor 110, a microphone 120 and a transmitter 180. Controller 100 may be a standalone devise not physically connected to implant 200. Sound processor 110 may be a central processing unit (CPU), a chip or any suitable computing or computational device. Sound processor 110 may be configured to process acoustical signals, captured by microphone 120, encode them and transmit the encoded signals to implant 200 to generate electrical and/or optical signals to be delivered to stimulate the cochlea nerve. Sound processor 110 may include an operating system, a memory and an executable code. Sound processor 110 may be configured to carry out methods described herein, for example, methods of selecting stimulations for a CI. Microphone 120 may be any suitable device known in the art configured to capture acoustic singles, for example, speech, music, singing and the like. Transmitter 180 may be any device that may be configured to transmit instructions and/or encoded signals (e.g., wirelessly using any known method) to a receiver 190 included in implant 200.

Implant 200 may include: receiver 190 configured to receive encoded signals from sound processor 110 via transmitter 180 and to transmit them to an electrical signal generator 192 and/or to an optical signal generator 194. In some embodiments, electrical signal generator 192 may be connected to an electrode 210 and optical signal generator 194 may be connected to an optrode (e.g., an optical stimulator) 220. In some embodiments, electrode 210 and optrode 220 may be integrated into one unit 205 configured to be implanted in the cochlea. Electrical signal generator 192 may include any electrical source configured to provide electrical signals to electrode 210. Electrode 210 may include one or more electrical wires connected to a plurality of electrical contacts 212, illustrated and discussed in detail with respect to FIG. 2. In some embodiments, electrical signal generator 192 may be configured to provide electrical signals to at least some of electrical contacts 212 based on encoded signals received from sound processor 110.

Figure 2:
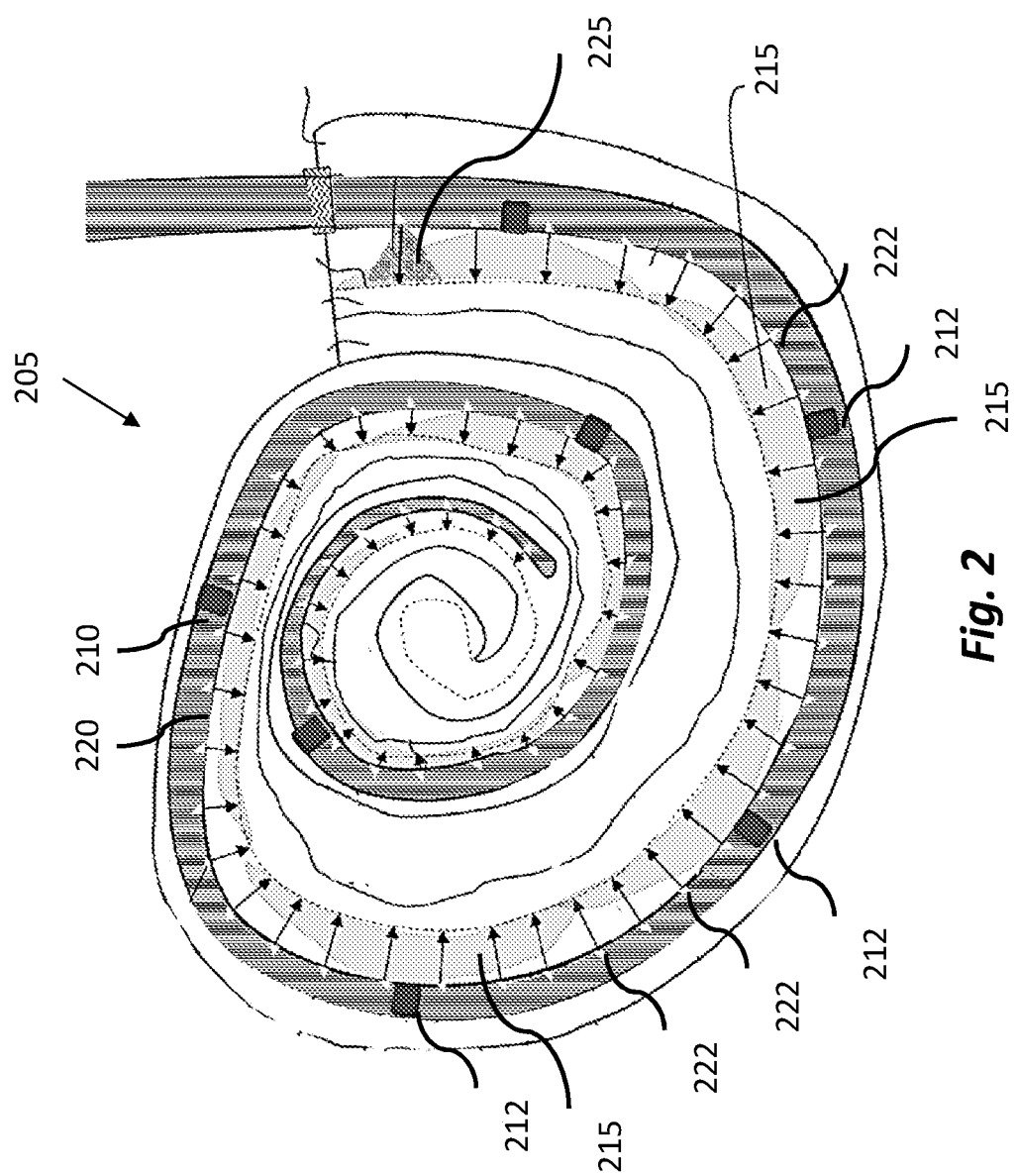
FIG. 2 shows an illustration of an implant integrated electrode and optrode according to some embodiments of the invention.

In some embodiments, optical signal generator 194 may be configured to generate optical signals and deliver the optical signals to a plurality of light emitters 222 included in optrode 220, illustrated and discussed in detail with respect to FIG. 2. In some embodiments, optical signal generator 194 may be an electrical source configured to provide electrical signals via a plurality of wires to light emitters 222 that may each include one or more photons generating elements, such as, LEDs, laser diodes and the like. Accordingly, optical signal generator 194 may provide electrical signals to at least some light emitters 222 according to instructions received from sound processor 110.

In some embodiments, optical signal generator 194 may be a photons generating source, such as laser diode and/or LEDs, configured to provide light (e.g., photons) via one or more waveguides (e.g., optical fibers or light guides) to light emitters 222 that may each include optical projection element, such as, lens, mirror, prism and the like. In some embodiments, optical generator 194 may provide light via at least some of the waveguides according to encoded signals received from sound processor 110.

Reference is now made to FIG. 2 which is an illustration of an implant 200 according to some embodiments of the invention. Implant 200 may include an electrode 210 connected to a plurality of electrical contacts 212 (via, for example, a plurality of electrical wires) and an optrode 220 connected to a plurality of light emitters 222. In some embodiments, integrated electrode and optrode unit 205 of implant 200 may be implanted inside the cochlea or along any other auditory nerve, such that, electrical contacts 212 and light emitters 222 are located along the cochlea or along the auditory nerve. As should be understood by one skilled in the art, the 7 electrical contacts and 50 light emitters illustrated in FIG. 2 are given as an example, only and the invention is not limited to any specific number of electrical contacts and light emitters.

In some embodiments, each electrical contact 212 may be configured to provide an electrical stimulation to a location along the cochlear nerve or along any other auditory nerve. Each electrical stimulation may have a current spread area 215 (illustrated in light grey) spreading from the electrode contact. The location of each electrical contact 212 may be determine as to provide a continuous coverage and stimulation along the cochlea or along the other auditory nerve. In some embodiments, current spread area 215 may stimulate neurons corresponding to about one octave in the acoustical spectrum. In some embodiments, light emitters 222 may be configured to provide optical stimulation to a location along the cochlear nerve or along any other auditory nerve. The light illuminated by each light source may spread over area 225 (illustrated in dark grey). In some embodiments, light spread area 225 may be narrower than current spread area 215, thus stimulating narrow cochlear nerve portion or narrow other auditory nerve portion. Accordingly, optical stimulation through light emitters 222 may provide higher stimulation resolution than electrical stimulation through the electrical contacts 212. However, the required energy to stimulate nerves is lower for electrical stimulation than for optical stimulation. Additionally, the conversion efficiency of electricity power to stimulation energy is lower for electrical stimulation than for optical stimulation. Therefore, a device according to embodiments of the invention may select to stimulate the cochlear nerve or other auditory nerve using an optimal selection of optical stimulation through the light emitters 222 and electrical stimulation through the electrical contacts 212, as to provide high resolution stimulation, as would have been conducted by using only optical stimulation, with less heat dissipation and energy consumption.

In some embodiments, device 10 (e.g., CI 10) may be configured to provide also opto-electrical stimulation. The opto-electrical stimulation may be conducted by generating at a substantially same location and at substantially the same time an electrical stimulation and an optical stimulation, such that each one of the electrical stimulation and the optical stimulation may have an intensity level which is below a stimulation level and the combined intensity level may be above the stimulation level of the cochlear nerve or other auditory nerve. Therefore, only at the location at which the optical stimulation may be given, the intensity level may reach the stimulation level. Accordingly, an opto-electrical stimulation is as accurate as an optical stimulation using less energy than optical stimulation alone.

Figure 3:
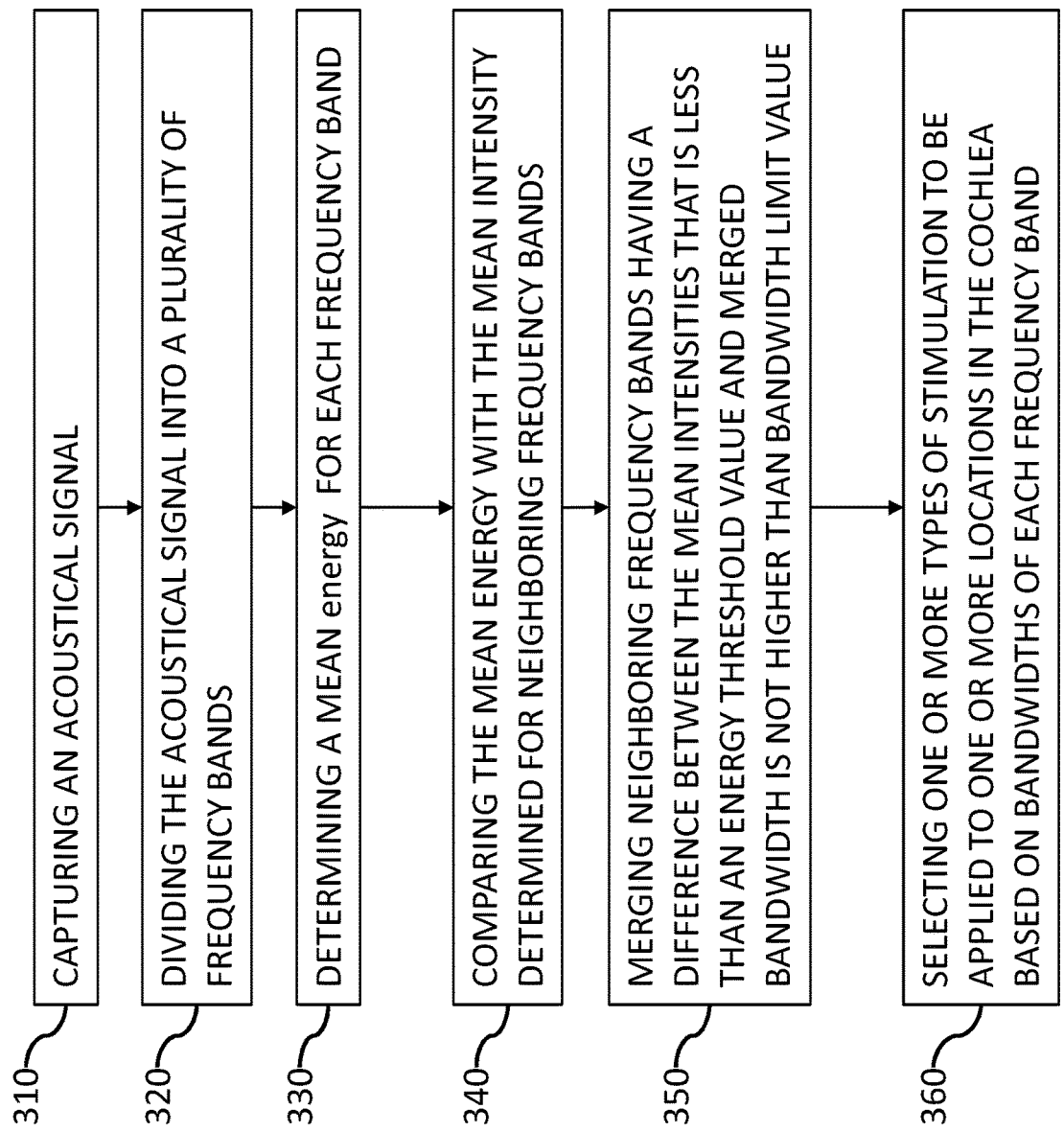
FIG. 3. is a flowchart of a method of selecting stimulations for a CI according to some embodiments of the invention.

Reference is now made to FIG. 3 which is a flowchart of a method of selecting stimulations for a CI or any other auditory nerve implant, according to some embodiments of the invention. The method of FIG. 3 may be conducted by system, such as, controller 100 (e.g., using sound processor 110) controlling an implant, such as, implant 200, or by any other suitable system. In step 310, an acoustical signal may be captured, for example, by one or more microphones 120. The acoustical signal may be analyzed/processed using any known methods, for example, the methods discussed hereinbelow with respect to FIGS. 6-8. In some embodiments, the acoustical signal may include, speech, music, singing and/or any acoustical signal hearable by the human ear. The acoustical signal recorded with the microphone(s) 20 may pass through a pre-emphasis filter that may boost the high frequencies of the signal, typically frequencies above 2 kHz in the frequency spectrum.

In step 320, the acoustical signal may be divided to a plurality of frequency bands. In some embodiments, the number of frequency bands may be determined based on the number of light emitters 222 included in the CI, as illustrated in FIG. 5B. For example, the acoustical signal may be divided to 20-50 frequency bands according to the number of light emitters 222. In some embodiments, number of frequency bands may be determined based on the number of electrical contacts 212 included in the implants. Accordingly, two initial bandwidths F may be determined:

(1) $\Gamma_{optical}$=CI spectrum/$N_{optical\ contacts}$
(2) $\Gamma_{electrical}$=bandwidth of frequencies correspond to neurons affected from the current spread of electrical stimulation.

Where CI spectrum, for example, CI spectrum illustrated in FIG. 5A, is determined as the entire frequency range that may be stimulated by a specific CI implanted in a specific patient. For example, when the lowest frequency that may be stimulated is 200 Hz and the highest frequency is 8000 Hz than the CI spectrum may be 200-8000. The CI spectrum may be measured for each specific patient after the implantation.

In some embodiments, the number of frequency bands may be determined by the maximal number of light emitters and/or electrical contacts included in the CI.

In some embodiments, the dividing step may be performed by a short-time Fourier transformation (STFT) of the acoustical signal, or by filtering the acoustical signal by a series of filters such as, but not limited to, gammatone-weighted filters with different center frequencies, or by a wavelet transformation of the acoustical signal.

In step 330, a mean acoustic energy may be determined for each frequency band, for example, for each $\Gamma_{optical}$.

In step 340, the mean acoustic energy of each band may be compared with the mean acoustic energy determined for neighboring frequency bands.

In step 350, neighboring frequency bands, having a difference between the mean energies that is less than an acoustic energy threshold value ($E_{threshold}$) may be merged into a new frequency band. In some embodiments, neighboring frequency bands (either merged or unmerged) may continue to be merged if the merged bandwidth is not larger than a bandwidth limit value $\Gamma_{limit}$, which may be predefined. In some embodiments $\Gamma_{limit}$ may be equal to $\Gamma_{electrical}$. In some embodiments, at least one of the energy threshold value ($E_{threshold}$) and bandwidth limit value ($\Gamma_{limit}$) may be determined for each person during the activation of device 10, using a calibration process. Accordingly, the acoustical signal may now be divided to uneven frequency bands that include both merged bands and unmerged bands, as illustrated in FIG. 5C.

FIGS. 5A-5C are illustrations of an acoustical frequency spectrum and the division of the spectrum into frequency bends in accordance with some embodiments of the present invention. FIG. 5A illustrates a bar showing a full hearing spectrum of human ear 20 Hz-20 kHz in comparison to an example for a CI spectrum 200 Hz-8 kHz. The CI spectrum is smaller than the full spectrum, for example, due to the location of the first and last light emitters 222 which is this specific example may not stimulate neurons corresponding to frequencies lower than 200 Hz and higher than 8 kHz. FIG. 5B illustrates a division of a CI spectrum to bands according to the number of light emitters 222 included in an implant (e.g., implant 200). FIG. 5C illustrates merged and unmerged bands of frequencies, according to some embodiments of the invention.

In step 360, one or more types of stimulation may be selected to be applied to one or more locations in a cochlea or a long other auditory nerve based on bandwidths of each frequency band. In some embodiments, the one or more types of stimulation may be selected from: electrical stimulation, optical stimulation and opto-electrical stimulation. In some embodiments, the one or more locations in cochlea or along other auditory nerve may correspond to specific frequencies of the acoustical signal, as discussed herein above.

In some embodiments, electrical stimulation may be selected for merged neighboring frequency bands. For example, if $\Gamma_{band}\approx\Gamma_{electrical}$ the selected band may be stimulated using an electrical contact of an electrode placed in the corresponding location in the cochlea. In some embodiments, electrical stimulation may be selected for merged neighboring frequency bands having a combined frequency bandwidth higher than a bandwidth threshold value $\Gamma_{threshold}$. The bandwidth threshold value $\Gamma_{threshold}$ may be determined based on $\Gamma_{electrical}$.

In some embodiments, optical stimulation and opto-electrical stimulation may be selected for the unmerged frequency bands. For example, if $\Gamma_{band}\approx\Gamma_{optical}$ the selected band may be stimulated using either optical stimulation or an opto-electrical stimulation. In some embodiments, the optical stimulation and opto-electrical stimulation may further be selected for merged frequency bands having a combined frequency bandwidth lower than a bandwidth threshold value $\Gamma_{threshold}$.

The opto-electrical stimulation may be conducted by generating at a substantially same location an electrical stimulation and an optical stimulation, such that each one of the electrical stimulation and the optical stimulation may have an intensity level which is below a stimulation level and the combined intensity level is above the stimulation level of the cochlear nerve. A method of calculating a probability to deliver a pulse in an opto-electrical stimulation is discussed in detail with respect to FIG. 8.

In some embodiments, a wavelength of the optical simulation may be selected to be between 400-1064 nm for optogenetics stimulation. In some embodiments, a wavelength of the optical simulation may be selected to be 1064-2500 nm for infrared neural stimulation.

In some embodiments, the method may further include generating the selected one or more types of stimulation at the one or more locations in cochlea using at least one of: one or more electrical contacts and one or more light emitters. In some embodiments, the generated selected one or more types of stimulation may provide the user with high quality hearing experience, that may allow for example, higher qualities of speech recognition and music appreciation than the ones provide to the users by commercially available implants.

Figure 4:
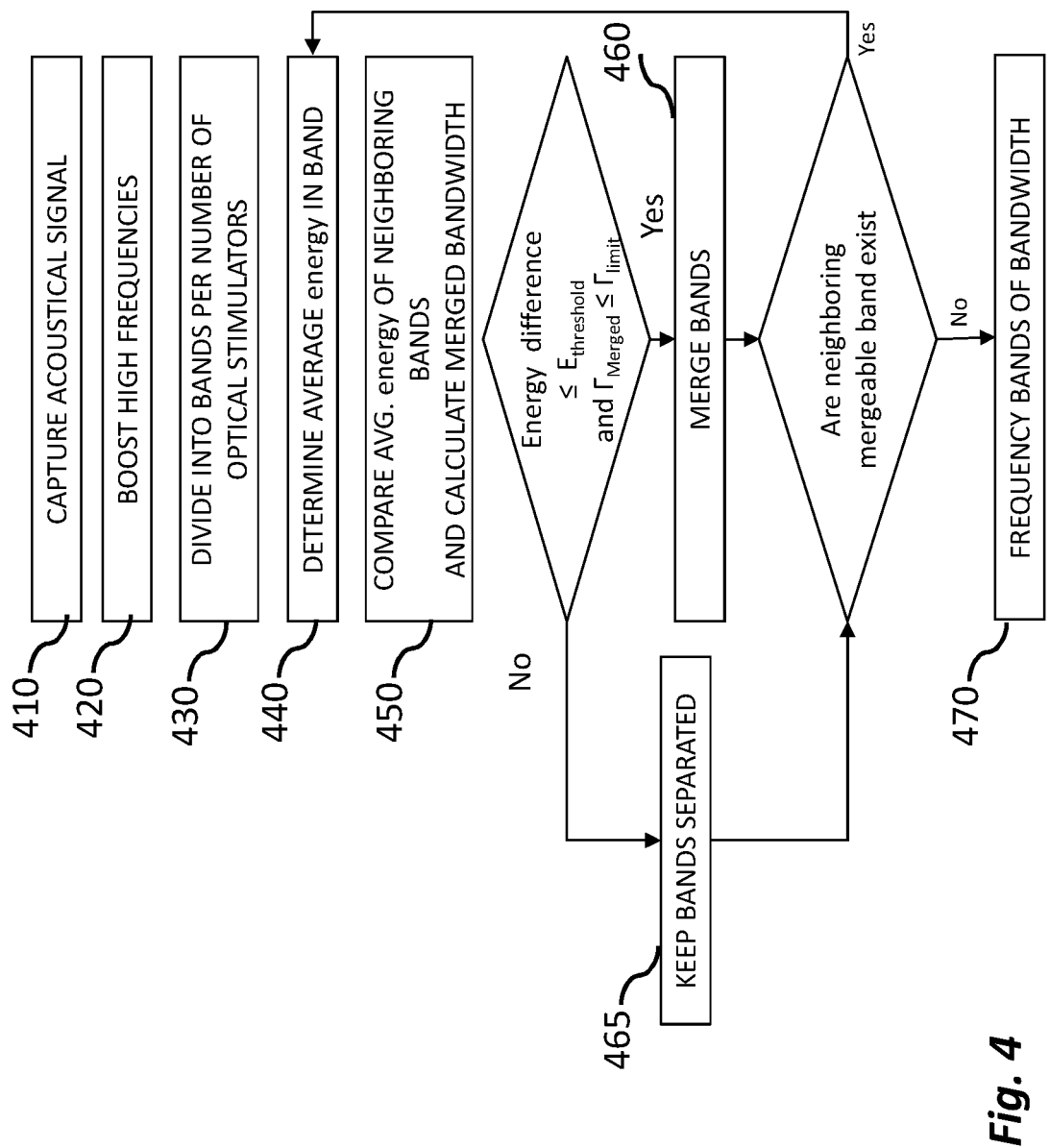
FIG. 4 is a flowchart of a method of selecting stimulations for a CI according to some embodiments of the invention.

Reference is now made to FIG. 4 which is a flowchart of a method of selecting stimulations for a CI according to some embodiments of the invention. The method of FIG. 4 may be conducted by system, such as, device 10, or by any other suitable system. In step 410 an acoustical signal may be captured. Step 410 may be substantially the same as step 310 disclosed herein above. In step 420, the high frequencies of the captured acoustical signal may be boosted (e.g., amplified).

In step 430, the acoustical signal may be divided into bands. The number of bands may be selected as the number of light emitters (e.g., light emitters 222) available in the CI, for example, device 10.

In step 440, the average acoustic energy for each band may be determined. Step 440 may be substantially the same as step 330 disclosed herein above. In step 450, the acoustic energy for each band may be compared with acoustic energies of neighboring frequency bands. In some embodiments, if the difference between the mean energies of the neighboring bands is less than the energy threshold ($E_{threshold}$) value and the merged bandwidth is not larger than the limit bandwidth ($\Gamma_{limit}$) value, the neighboring bands may be merged, in step in step 460. If the difference between the mean energies of the neighboring bands is more than the energy threshold value ($E_{threshold}$), or the merged bandwidth is larger than the limit bandwidth value ($\Gamma_{limit}$), the neighboring bands may not be merged, in step 465.

Figure 6:
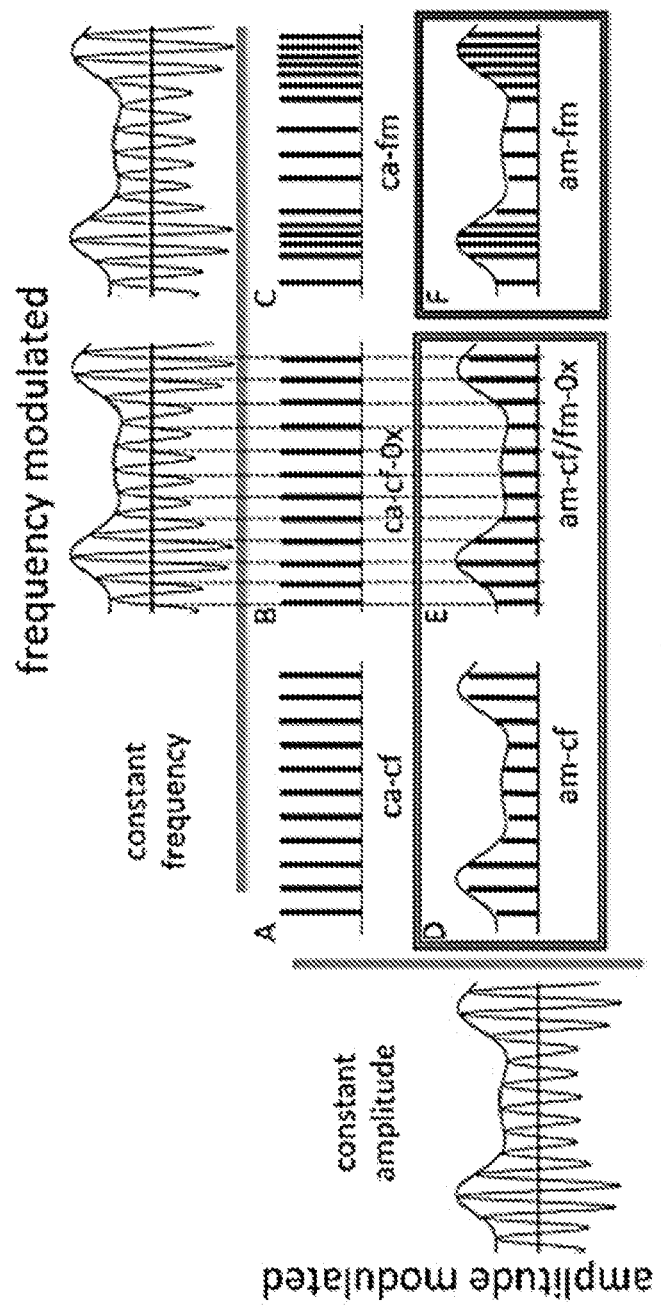
FIG. 6 shows examples for coding acoustical information as known in the art[?]

Reference is now made to FIG. 6 which shows different strategies, known in the art, for coding acoustical information. The solutions depicted in panels A and B of FIG. 6 are not practical for CIs and are presented for completeness. A train of biphasic pulses with constant amplitude (ca) and constant frequency (cf) has limited use because only single amplitudes can be encoded by the amplitude of the pulses and one single frequency by the pulse repetition rate (panel A of FIG. 6) or the stimulation site along the cochlea. Additional timing information can be added if the times are considered at which the carrier of the acoustical signal has zero crossings and the slope of the carrier is positive (panel B of FIG. 6). The E of the acoustical signal can be used to modulate a constant carrier (panel D of FIG. 6).

To avoid simultaneous stimulation at neighboring electrodes the carrier pulses are presented at adjacent electrodes in a continuous interleaved pattern (CIS). The latter strategy is commonly used in coding strategies of contemporary CIs. Some codes adopt the approach shown in panel E of FIG. 6. A carrier is amplitude modulated with the E of the acoustical signal. The zero crossings of the TFS are then used to provide additional timing information. Coding strategies depicted in panels C and F of FIG. 6 have not been implemented in CI today. TFS is also included in the n-of-m coding strategy (n number of frequencies are selected of m possible frequencies) and by implementing virtual channels (stimulation between two electrode contacts by electrical field superposition).

Figure 7:
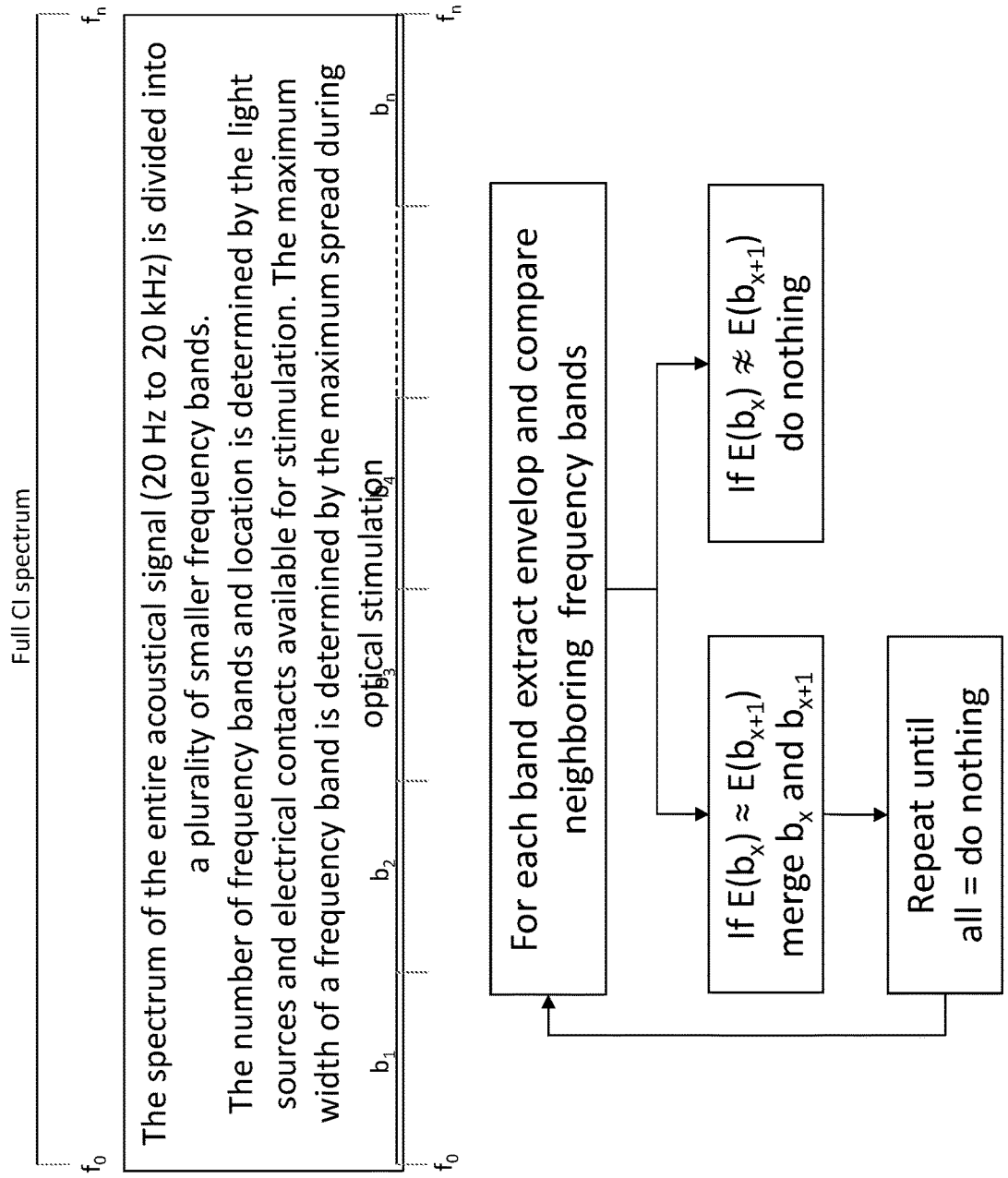
FIG. 7 is a flowchart of a method of selecting a width of the frequency band according to some embodiments of the invention.

Reference is now made to FIG. 7 which is a flowchart of selecting a width of the frequency band according to some embodiments of the invention. A frequency band may be selected to include a limited range of frequencies with the same or similar amplitude. The frequency range may be typically characterized by its lowest and its highest frequency. To process the acoustic information in a CI, the CI spectrum may be divided into a plurality of smaller frequency bands. The number of frequency bands may be determined by the maximal number of light emitters (e.g., emitters 222) and electrical contacts (e.g., electrical contacts 212) available for stimulation. The separation into a plurality of frequency bands may be achieved by a short-time Fourier Transformation (STFT) of the signal, or by filtering the acoustical signal by a series of filters such as, but not limited to, gammatone-weighted filters with different center frequencies, or by a wavelet transformation of the signal. Each frequency band or scaling factor may be then separated into its envelope (E; frequencies which are below 50 Hz), periodicity (P; frequencies which are between 50 and 500 Hz), and temporal fine structure (TFS; frequencies which are above 500 Hz). The definition of E, P and TFS is adopted from the literature.

In some embodiments, the loudness of the signal may be mapped according to a nonlinear function that describes the relation between the sound level (p) at the outer ear canal and the corresponding rate of action potentials (R) that can be recorded from a single auditory nerve. For the coding strategy, the energy in a short time segment of the spectrogram of the acoustic signal is extracted for a selected frequency band. Similarly, the energy may be extracted from the filtered signal. For example, the length of one time segment corresponded to 0.3 msec. Equation 3 is used to convert the energy into a normalized rate of the interval [0,1]. (3)

$$R = A_0 + \frac{A_1 * d^2}{A_2^2 + d^{2'}}$$

where the variables denote the following:
$A_0$=the spontaneous discharge rate of the primary afferent,
$A_1$=the maximum increase of the discharge rate,
$A_2$=the sound pressure of the half maximum discharge rate,
$A_3$=the sound pressure at which nonlinear behavior occurs, $A_4$=the exponent of the power-law slope in the nonlinear region,
p=the sound pressure level at the tympanic membrane,
R=the mean discharge rate,
and d is $$d = \left[ \frac{A_3^{\left(\frac{1}{A_4}-1\right)} * p^{1/A_4}}{A_3^{\left(\frac{1}{A_4}-1\right)} + p^{\left(\frac{1}{A_4}-1\right)}} \right]^{A_4}.$$

The equation includes cochlear nonlinearities and depends on five critical parameters, the spontaneous rate ($A_0$), the maximum rate ($A_1$), the threshold for stimulation ($A_2$), the level for nonlinear behavior ($A_3$), and a value describing the slope after the level for nonlinear behavior ($A_4$). The parameter $A_0$ shifts the curve towards larger values. The maximum rate $A_1$ limits the maximum rate to the number selected. The level for threshold has large effects on the mapping. Low threshold values result in a fast increase in the rate and quick saturation, whereas large threshold values slow the increase in rate, but limit the maximum achievable rate. Smaller effects are seen from the parameters $A_3$ and $A_4$. Default values are selected ($A_0$=0; $A_1$=1; $A_2$=20; $A_3$=50; $A_4$=0.5), which must be adjusted individually during later session with the CI user. For the calculation of the normalized rate with the fixed parameters $A_0$=0 and $A_1$=1 the rate R will be in the interval [0,1]. For further calculations the R is called $P_{power}$.

In some embodiments, the method may include the extraction of TFS and ITS coding. In some embodiments, the auditory system of animals with normal cochlear function, it has been shown that the phase is encoded on the auditory nerve by the timed occurrence of action potentials (phase-locking). After an action potential is generated, the probability for another action potential is maximum at integer numbers of cycles following the last action potential. Our code has been developed similarly. In its simplest version, at the occurrence of a pulse, a multiplier $P_{phase}$ is set to 0 and increases over the time of 1/(center frequency) of the selected frequency band in a linear or nonlinear fashion to 1. At each integer number of the cycle times $P_{phase}$ is reset to 0. $P_{power}$ then modified by multiplying it by $P_{phase}$, which is a number of the interval [0,1]*$w_{phase}$. The multiplier $w_{phase}$ is a factor that can increase or decrease the phase effect. For the initial setting this weighing factor $w_{phase}$ is selected to be 1.

Figure 8:
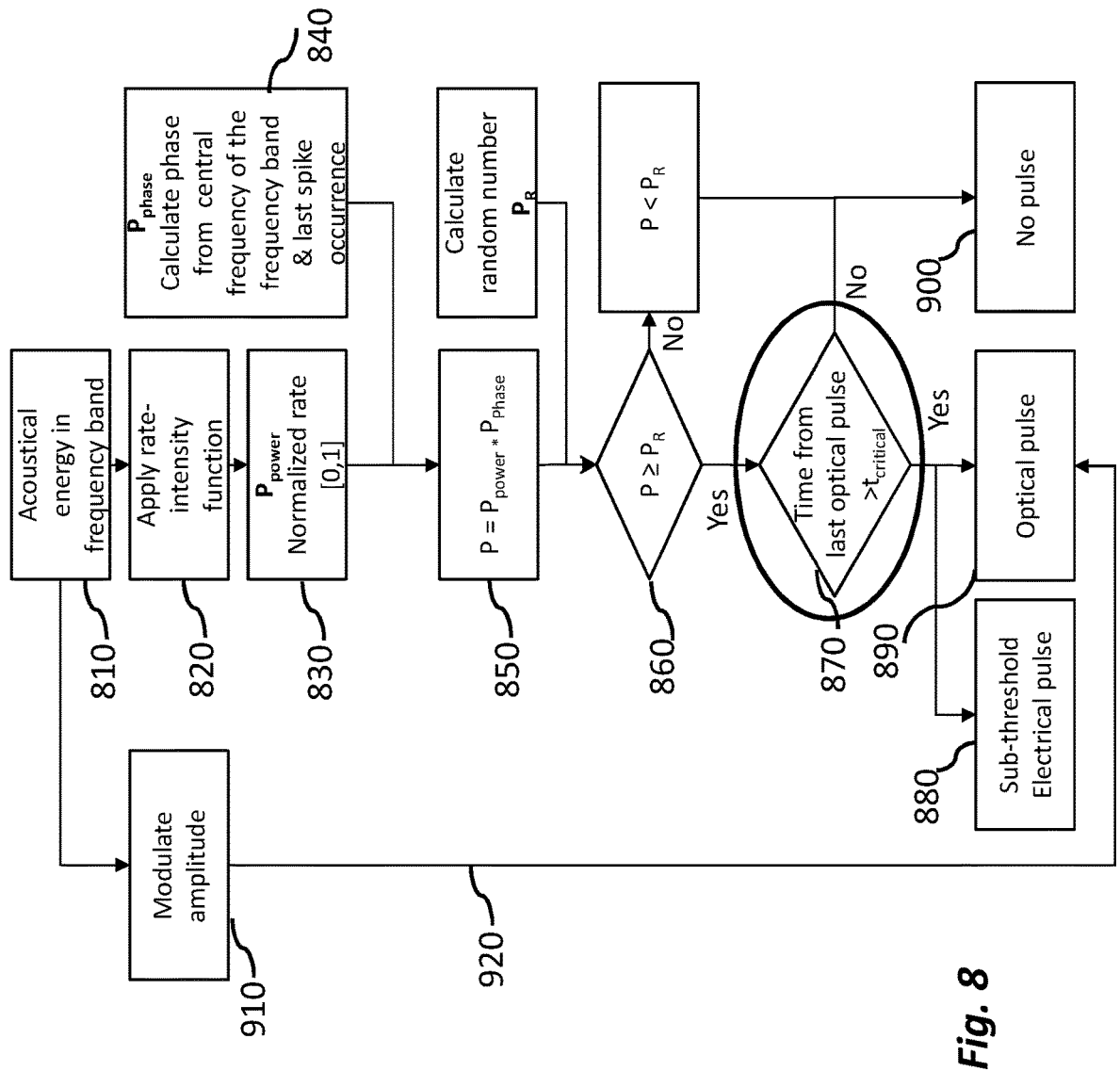
FIG. 8 is a flowchart of a method of determining a probability to deliver a pulse according to some embodiments of the invention.

Reference is now made to FIG. 8 which is a flowchart of a method of calculating a probability to deliver a pulse in an opto-electrical stimulation embodiment of the invention. In some embodiments, the method may include a decision to deliver the pulse. $P_{power}$ and $P_{phase}$ may be determined (in steps 830 and 840) for each band for time segment and may be used to calculate P (P=$P_{power}$*$P_{phase}$) in step 850. The number P may be then compared with a random number $P_R$ [0,1]d, in step 860. The series of random numbers may have a Poisson-like distribution. Only when $P_{power}$ may be larger than the random number a pulse may be delivered. Step 870 The energy derived from the calculations may also be used to directly modulate the amplitude of the resulting pulse train.

In some embodiments, the occurrence of the last pulse and the center frequency of the selected frequency band may also affect the probability to choose an electrical or optical pulse to be delivered, steps 840, 850, 860 and 870

In some embodiments, the factors that may determine whether a pulse (optical or electrical) should be delivered depend on the energy of the acoustic signal as described in steps 810-860. In some embodiments, for optical stimulation and for opto-electrical stimulation, the time from last optical pulse may be compared to a critical time $t_{critical}$ and a decision whether a new stimulation pulse may be delivered, may be made in steps 870, 880, 890 and 900.

In some embodiments the stimulation pulse may be modulated by the amplitude or energy of the acoustical signal, step 910 and 920. In opto-electrical stimulation embodiment the intensity of the electrical stimulation pulse may be below the stimulation threshold and may be independent from the acoustical energy in the frequency band, while the optical stimulation intensity is supra threshold and may be dependent or modulated by the intensity or energy of the acoustical energy in frequency band, steps 910, 920, 880 and 890.

The invention claimed is:

1. A method of selecting stimulations for a cochlear implant, comprising:
   capturing an acoustical signal;
   dividing the acoustical signal into a plurality of frequency bands;
   determining a mean acoustical energy for each frequency band;
   for each frequency band:
   comparing the mean acoustical energy with the mean acoustical energy determined for neighboring frequency bands;
   merging neighboring frequency bands having a difference between the mean acoustical energies that is less than an acoustical energy threshold value and merging neighboring frequency bands if the merged frequency bands have a bandwidth lower or equal to a bandwidth limit value, wherein the bandwidth limit value is equal to a bandwidth of frequencies corresponding to neurons effected from the current spread of electrical stimulation;
   selecting one or more types of stimulation to be applied to one or more locations in a cochlea based on bandwidths of each frequency band,
   wherein the one or more types of stimulation are selected from electrical stimulation, optical stimulation and opto-electrical stimulation, and
   selecting electrical stimulation for merged neighboring frequency bands having a combined frequency bandwidth higher than a bandwidth threshold value, and
   selecting optical and/or opto-electrical stimulation for merged and unmerged bands, and
   wherein a number of frequency bands and locations are determined by the light emitters and electrical contacts available for stimulation,
   wherein the maximum width of the frequency band is determined by the maximum spread during optical stimulation, and
   wherein the one or more locations in the cochlea correspond to specific frequencies of the acoustical signal.

2. The method according to claim 1, wherein selecting one of: optical stimulation and opto-electrical stimulation is for merged frequency bands having a combined frequency bandwidth lower than a bandwidth threshold value.

3. The method according to claim 1, wherein the opto-electrical stimulation comprises generating at a substantially same location an electrical stimulation and an optical stimulation, wherein each one of the electrical stimulation and the optical stimulation has an intensity level which is below a stimulation level.

4. The method according to claim 1, wherein a wavelength selected for optical simulation is 400-1064 nm for optogenetics stimulation.

5. The method according to claim 1, wherein a wavelength selected for optical simulation is 1064-2500 nm for infrared neural stimulation.

6. A method of generating stimulations for a cochlear implant, comprising:
  capturing an acoustical signal;
  dividing the acoustical signal into a plurality of frequency bands;
  determining a mean acoustical energy for each frequency band;
  for each frequency band, comparing the mean acoustical energy with the mean acoustical energy determined for neighboring frequency bands;
    merging neighboring frequency bands having a difference between the mean acoustical energy that is less than an acoustical energy threshold value and merging neighboring frequency bands if the merged frequency bands have a bandwidth lower or equal to a bandwidth limit value, wherein the bandwidth limit value is equal to a bandwidth of frequencies corresponding to neurons effected from the current spread of electrical stimulation;
  selecting one or more types of stimulation to be applied to one or more locations in a cochlea based on bandwidths of each frequency band;
  wherein the one or more types of stimulation are selected from electrical stimulation, optical stimulation and opto-electrical stimulation, and
  selecting electrical stimulation for merged neighboring frequency bands having a combined frequency bandwidth higher than a bandwidth threshold value; and
  selecting optical stimulation and/or opto-electrical stimulation for the merged and unmerged bands,
  wherein a number of frequency bands and locations are determined by the light emitters and electrical contacts available for stimulation,
  wherein the maximum width of the frequency band is determined by the maximum spread during optical stimulation, and
  wherein the one or more locations in the cochlea correspond to specific frequencies of the acoustical signal.

7. A method of selecting stimulations for an auditory implant, comprising:
  capturing an acoustical signal;
  dividing the acoustical signal into a plurality of frequency bands;
  determining a mean acoustical energy for each frequency band;
  for each frequency band:
  comparing the mean acoustical energy with the mean acoustical energy determined for neighboring frequency bands;
  merging neighboring frequency bands having a difference between the mean acoustical energies that is less than an acoustical energy threshold value and merging neighboring frequency bands if the merged frequency bands have a bandwidth lower or equal to a bandwidth limit value, wherein the bandwidth limit value is equal to a bandwidth of frequencies corresponding to neurons effected from the current spread of electrical stimulation;
  selecting one or more types of stimulation to be applied to one or more locations along an auditory nerve based on bandwidths of each frequency band,
  wherein the one or more types of stimulation are selected from electrical stimulation, optical stimulation and opto-electrical stimulation, and
  selecting electrical stimulation for merged neighboring frequency bands having a combined frequency bandwidth higher than a bandwidth threshold value,
  selecting optical stimulation and/or opto-electrical stimulation for the merged and unmerged bands,
  wherein a number of frequency bands and locations are determined by the light emitters and electrical contacts available for stimulation,
  wherein the maximum width of the frequency band is determined by the maximum spread during optical stimulation, and
  wherein the one or more locations along the auditory nerve correspond to specific frequencies of the acoustical signal.

* * * * *